United States Patent
Carroll et al.

(10) Patent No.: US 8,926,369 B2
(45) Date of Patent: Jan. 6, 2015

(54) ELECTRICAL CONNECTOR FOR SUBSTRATE HAVING CONDUCTIVE TRACKS

(71) Applicant: LifeScan Scotland Limited, Inverness, Inverness-shire (GB)

(72) Inventors: Gary Carroll, Iverness (GB); Ivan Confield, Iverness (GB); Luca Valsecchi, Monza (IT); Michele Sala, Monza (IT); Maurizio Volpe, Monza (IT); Roberto Beretta, Monza (IT); John Nelson, Iverness (GB)

(73) Assignee: LifeScan Scotland Limited, Inverness (GB)

( * ) Notice: Subject to any disclaimer, the term of this patent is extended or adjusted under 35 U.S.C. 154(b) by 99 days.

(21) Appl. No.: 13/722,983

(22) Filed: Dec. 20, 2012

(65) Prior Publication Data

US 2014/0179151 A1    Jun. 26, 2014

(51) Int. Cl.
| H01R 13/648 | (2006.01) |
| H01R 12/61 | (2011.01) |
| H01R 13/66 | (2006.01) |
| G01N 33/487 | (2006.01) |
| H01R 12/71 | (2011.01) |

(52) U.S. Cl.
CPC .......... *H01R 12/613* (2013.01); *H01R 2201/12* (2013.01); *H01R 13/6683* (2013.01); *G01N 33/48771* (2013.01); *H01R 2201/20* (2013.01); *H01R 12/714* (2013.01)
USPC .......... 439/630; 439/489; 204/403.02; 422/50

(58) Field of Classification Search
USPC .......... 439/630, 489, 488, 909, 149; 204/406, 204/435, 403.02, 403.14, 403.03; 422/50
See application file for complete search history.

(56) References Cited

U.S. PATENT DOCUMENTS

| 6,039,599 | A | * | 3/2000 | Benjamin et al. | ............. 439/489 |
| 6,135,809 | A | * | 10/2000 | Asakawa | ....................... 439/489 |
| 6,616,819 | B1 | * | 9/2003 | Liamos et al. | ........... 204/403.02 |
| 6,749,740 | B2 | * | 6/2004 | Liamos et al. | ................ 205/792 |
| 6,942,518 | B2 | | 9/2005 | Liamos et al. | |

(Continued)

FOREIGN PATENT DOCUMENTS

| EP | 1 382 968 A1 | 1/2004 |
| EP | 1431758 A1 | 6/2004 |

(Continued)

OTHER PUBLICATIONS

International Search Report and Written Opinion issued in corresponding International Application No. PCT/GB2013/053354, dated May 8, 2014, 19 pages.

*Primary Examiner* — Gary Paumen

(57) ABSTRACT

An electrical connector can receive a substrate having conductive tracks. The connector includes a housing with a port and at least one alignment feature that together define a direction of insertion. At least three function pins mounted to the housing each include contacts that electrically connect to one of the conductive tracks of a substrate inserted in the connector. A sense pin mounted to the housing has a contact that electrically connects to at least one of the conductive tracks of an inserted substrate. The sense pin can include a plurality of electrically-connected segments, each segment extending substantially parallel or substantially perpendicular to the direction of insertion of the substrate. Systems and methods for detecting an analyte in a bodily-fluid sample are also described.

17 Claims, 10 Drawing Sheets

(56) References Cited

U.S. PATENT DOCUMENTS

| | | | |
|---|---|---|---|
| 7,488,216 B2* | 2/2009 | Cho | 439/638 |
| 7,527,528 B2* | 5/2009 | Yu et al. | 439/630 |
| 7,731,539 B2* | 6/2010 | Ooaku | 439/630 |
| 7,775,826 B1* | 8/2010 | Wang | 439/489 |
| 7,896,670 B1* | 3/2011 | Gao et al. | 439/159 |
| 7,914,335 B2 | 3/2011 | Stafford et al. | |
| 7,934,946 B2* | 5/2011 | Alejandro et al. | 439/489 |
| 8,066,858 B2 | 11/2011 | Wang et al. | |
| 8,083,993 B2 | 12/2011 | Groll | |
| 8,123,538 B2* | 2/2012 | Xu et al. | 439/188 |
| 8,277,238 B2* | 10/2012 | Matsumoto et al. | 439/188 |
| 8,398,416 B2* | 3/2013 | Tseng | 439/188 |
| 8,500,472 B2* | 8/2013 | Shimoyama et al. | 439/188 |
| 8,585,427 B2* | 11/2013 | Ukawa et al. | 439/377 |
| 2003/0203498 A1 | 10/2003 | Neel et al. | |
| 2004/0161965 A1* | 8/2004 | Bricaud et al. | 439/489 |
| 2005/0142949 A1* | 6/2005 | Fang et al. | 439/630 |
| 2006/0063422 A1* | 3/2006 | Lu et al. | 439/489 |
| 2006/0091006 A1 | 5/2006 | Wang et al. | |
| 2006/0223376 A1* | 10/2006 | Chang et al. | 439/630 |
| 2007/0072482 A1* | 3/2007 | Fujii et al. | 439/489 |
| 2008/0132110 A1* | 6/2008 | Lai et al. | 439/489 |
| 2009/0029479 A1 | 1/2009 | Docherty et al. | |
| 2009/0078588 A1 | 3/2009 | Lin et al. | |
| 2009/0095623 A1 | 4/2009 | Boiteau et al. | |
| 2010/0210145 A1* | 8/2010 | Wang et al. | 439/630 |
| 2011/0057671 A1 | 3/2011 | Welsh et al. | |
| 2011/0139635 A1 | 6/2011 | Huang et al. | |
| 2011/0195598 A1* | 8/2011 | Panella et al. | 439/488 |

FOREIGN PATENT DOCUMENTS

| | | |
|---|---|---|
| WO | 2004106885 A2 | 12/2004 |
| WO | 2010091793 A2 | 8/2010 |
| WO | WO 2011/094315 A1 | 8/2011 |

* cited by examiner

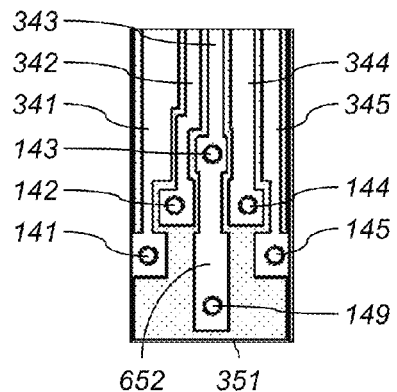 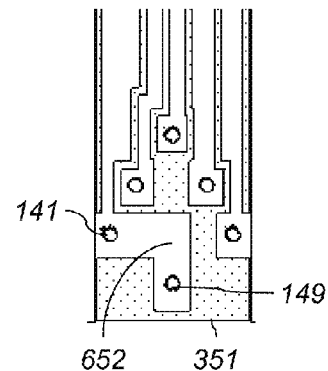 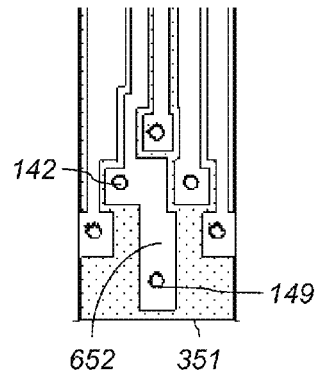
FIG. 7　　　FIG. 8　　　FIG. 9
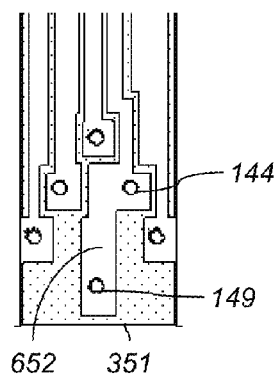 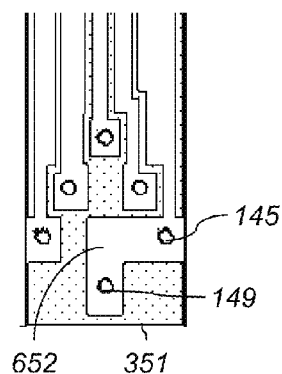
FIG. 10　　　FIG. 11

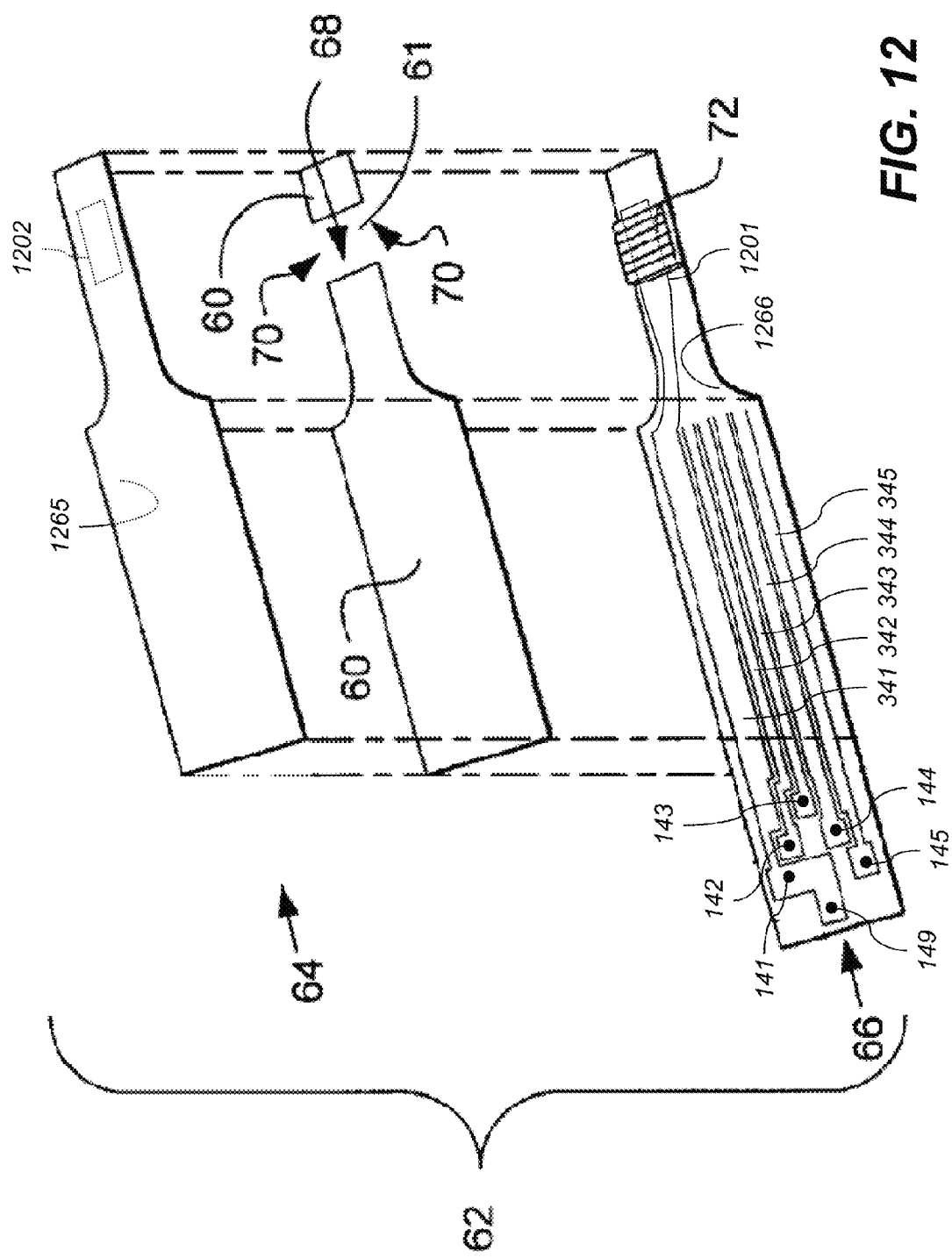

ELECTRICAL CONNECTOR FOR SUBSTRATE HAVING CONDUCTIVE TRACKS

TECHNICAL FIELD

The present application relates to substrates having conductive tracks, connectors for making electrical connection with such substrates, and ways of using such connectors and substrates. In various aspects, such substrates are adapted for use in monitoring blood glucose.

BACKGROUND

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbAlc concentrations in a sample of a bodily fluid such as urine, blood, plasma, interstitial fluid, or other fluids found in the bodies of humans or other organisms. Such determinations can be achieved using an analytical test strip and test meter combination.

BRIEF DESCRIPTION OF THE INVENTION

According to one aspect, there is provided an electrical connector adapted to receive a first substrate of a selected width, the first substrate having a plurality of conductive tracks disposed over a face surface of the first substrate, the electrical connector comprising:
  a) a housing comprising:
    i) a port; and
    ii) at least one first alignment feature spaced apart from the port to define a direction of permitted insertion of the first substrate into the electrical connector;
  b) at least three function pins mounted to the housing, each said function pin having a respective contact arranged to electrically connect to a respective one of the plurality of conductive tracks of the first substrate inserted in the electrical connector, the respective contacts being arranged between the port and the at least one first alignment feature in the direction of permitted insertion;
  c) a sense pin mounted to the housing, the sense pin having a contact adapted to electrically connect to at least one of the plurality of conductive tracks of the first substrate when inserted a predetermined distance into the electrical connector; and
  the sense pin further including a plurality of electrically-connected segments, at least one of said segments being mechanically mounted to the housing, each said segment extending substantially parallel or substantially perpendicular to the direction of permitted insertion of said first substrate.

According to another aspect, there is provided a system for detecting an analyte in a bodily-fluid sample, said system comprising:
  a) a controller;
  b) a test strip having a sample-receiving chamber and a plurality of conductive tracks electrically discontinuous from each other, each conductive track arranged at least partially on a first side of said test strip and at least partially adjacent to the sample-receiving chamber;
  c) an electrical connector comprising:
    i) a housing with a port adapted to receive the test strip inserted in a direction of permitted insertion;
    ii) three or more function pins mounted to the housing, each said function pin having a respective contact arranged to electrically connect to a respective one of the plurality of conductive tracks of the test strip inserted in the electrical connector; and
    iii) a sense pin mounted to the housing and having a contact adapted to electrically connect to one of the respective ones of the plurality of conductive tracks of the test strip inserted in the electrical connector, the contact of said sense pin being arranged opposite the port along the direction of permitted insertion;
  d) a continuity sensor adapted to detect an electrical connection between the sense pin and at least one of the function pins and provide an indication of which function pin(s) are electrically connected to the sense pin; and
  e) a storage unit storing a selected continuity configuration and a corresponding selection of two or more of the function pins;
  wherein the controller is adapted to automatically:
    i) in response to the continuity sensor, compare the provided indication to the stored selected continuity configuration; and
    ii) if the provided indication corresponds to the stored selected continuity configuration, activate the ones of the function pins indicated by the stored corresponding selection to apply a test electrical signal across the sample-receiving chamber, and measure a result electrical signal to detect the analyte in the sample-receiving chamber.

According to another aspect, there is provided a method for determining an analyte in a bodily-fluid sample, the method comprising:
  receiving an analytical test strip using a electrical connector of a test meter such that at least three conductive tracks exposed on a first side of the analytical test strip make electrical contact with respective function pins of the electrical connector and at least one of the conductive tracks further makes electrical contact with a sense pin of the electrical connector, the analytical test strip including a sample-receiving chamber adapted to receive the bodily-fluid sample;
  sensing, using a controller of the test meter, electrical continuity between the sense pin and a first one of the function pins;
  when continuity is sensed, the controller comparing an identity of the first one of the function pins to stored continuity-configuration information;
  if the identity of the first one of the function pins corresponds to the stored continuity-configuration information, the controller automatically applying a selected electrical signal to selected ones of the function pins indicated by the stored continuity-configuration information and measuring a result electrical signal; and
  the controller automatically processing the result electrical signal to detect whether a bodily-fluid sample has been applied to the sample-receiving chamber and, if so, to determine the analyte in the applied bodily-fluid sample.

According to another aspect, there is provided an electrical connector adapted to receive a first substrate of a selected width, the first substrate having a plurality of conductive tracks disposed over a face surface of the first substrate, the electrical connector comprising:
  a) a housing comprising:
    i) a port; and
    ii) at least one first alignment feature spaced apart from the port to define a direction of permitted insertion of the first substrate into the electrical connector;
  b) at least three function pins mounted to the housing, each said function pin having a respective contact arranged to electrically connect to a respective one of the plurality of conductive tracks of the first substrate inserted in the electrical connector, the respective contacts being arranged between the port and the at least one first alignment feature in the direction of permitted insertion; and c) a sense pin mounted to the housing, the sense pin having a contact adapted to electrically connect to at least one of the plurality of conductive tracks of the first substrate when inserted a predetermined distance into the electrical connector;

wherein said contact of said sense pin is arranged between said respective contacts of two of said at least three function pins in a direction substantially perpendicular to the direction of permitted insertion.

Advantageously, effective electrical connection can be provided between a test strip and a controller, e.g., to detect analytes in bodily-fluid samples. In addition, various types of test strips can be separately utilized in a test meter, or only those test strips with a selected continuity configuration. The incorporation of at least three electrodes and corresponding conductive tracks further provides improved measurement of samples, e.g., by measuring hematocrit separately from glucose in a blood sample.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIGS. 7-11 show layouts of conductive tracks on substrates according to various aspects;

FIG. 12 is an exploded perspective view of a test strip;

The attached drawings are for purposes of illustration and are not necessarily to scale.

DETAILED DESCRIPTION OF THE INVENTION

The following relates to certain exemplary embodiments of a connector for use with a substrate, such as an analytical test strip used for determining the presence of an analyte (e.g., blood glucose), as well as to methods of use of the connector and systems for use therewith. Throughout the course of discussion certain terms are used in order to provide a suitable frame of reference with regard to the accompanying drawings. These terms, however, should not be stringently interpreted to influence scope, including those of the appended claims, unless where specifically indicated. In addition and in the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems or methods described herein. Other aspects of such algorithms and systems, and hardware or software for producing and otherwise processing the signals involved therewith, not specifically shown or described herein, are selected from such systems, algorithms, components, and elements known in the art. Given the systems or methods as described herein, software not specifically shown, suggested, or described herein that is useful for implementation of any aspect is conventional and within the ordinary skill in such arts.

Throughout this disclosure, any discussion of a feature being between two other features in a particular direction does not require that feature be on a straight line between the two other features. For example, the stem of a capital Y is between the upper-left and upper-right diagonal segments of the Y in a horizontal direction, even though the stem is below any straight line between those segments.

Figure 1:
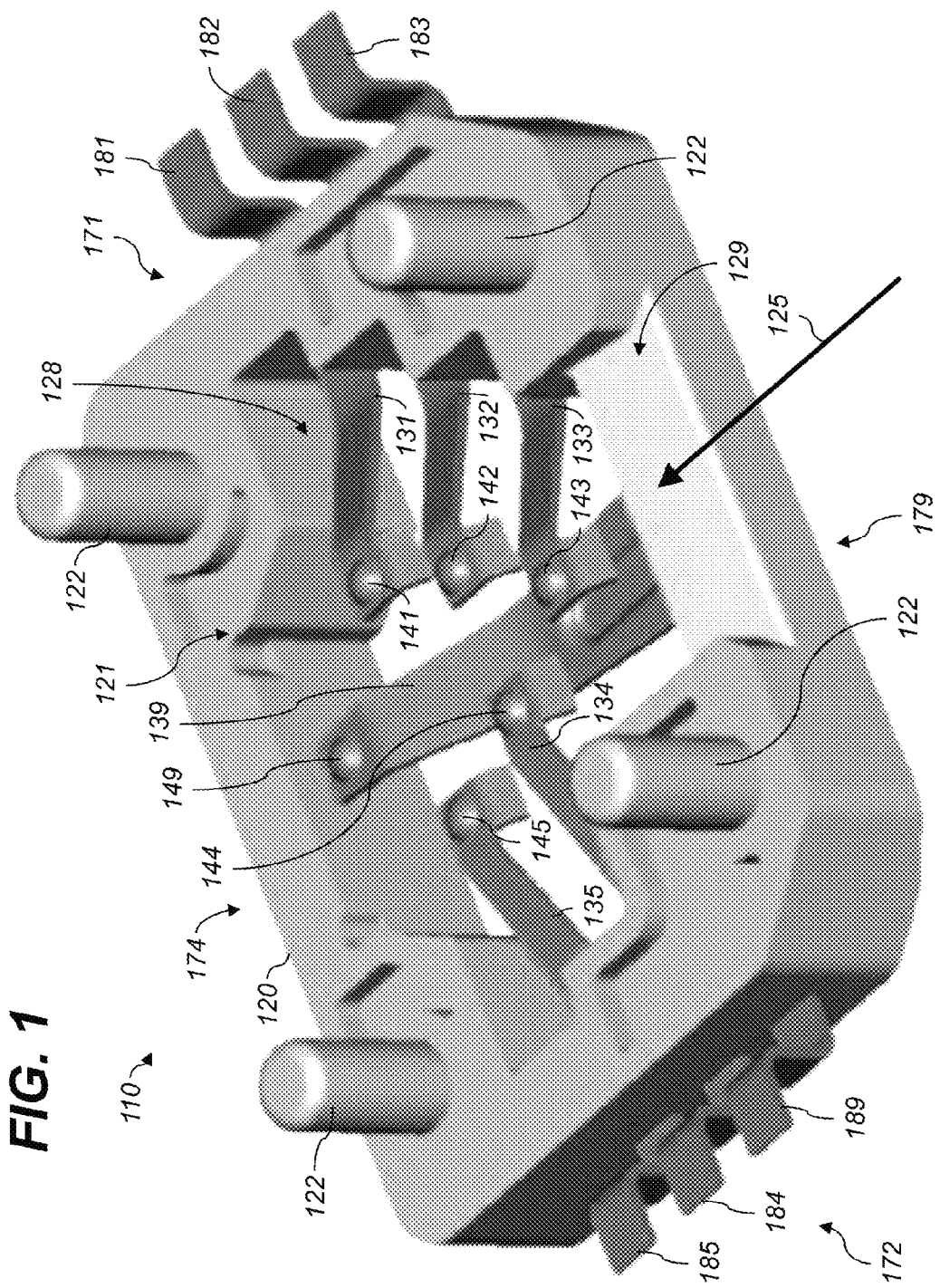
FIG. 1 is a top perspective view of a connector according to an exemplary embodiment.
Figure 3:
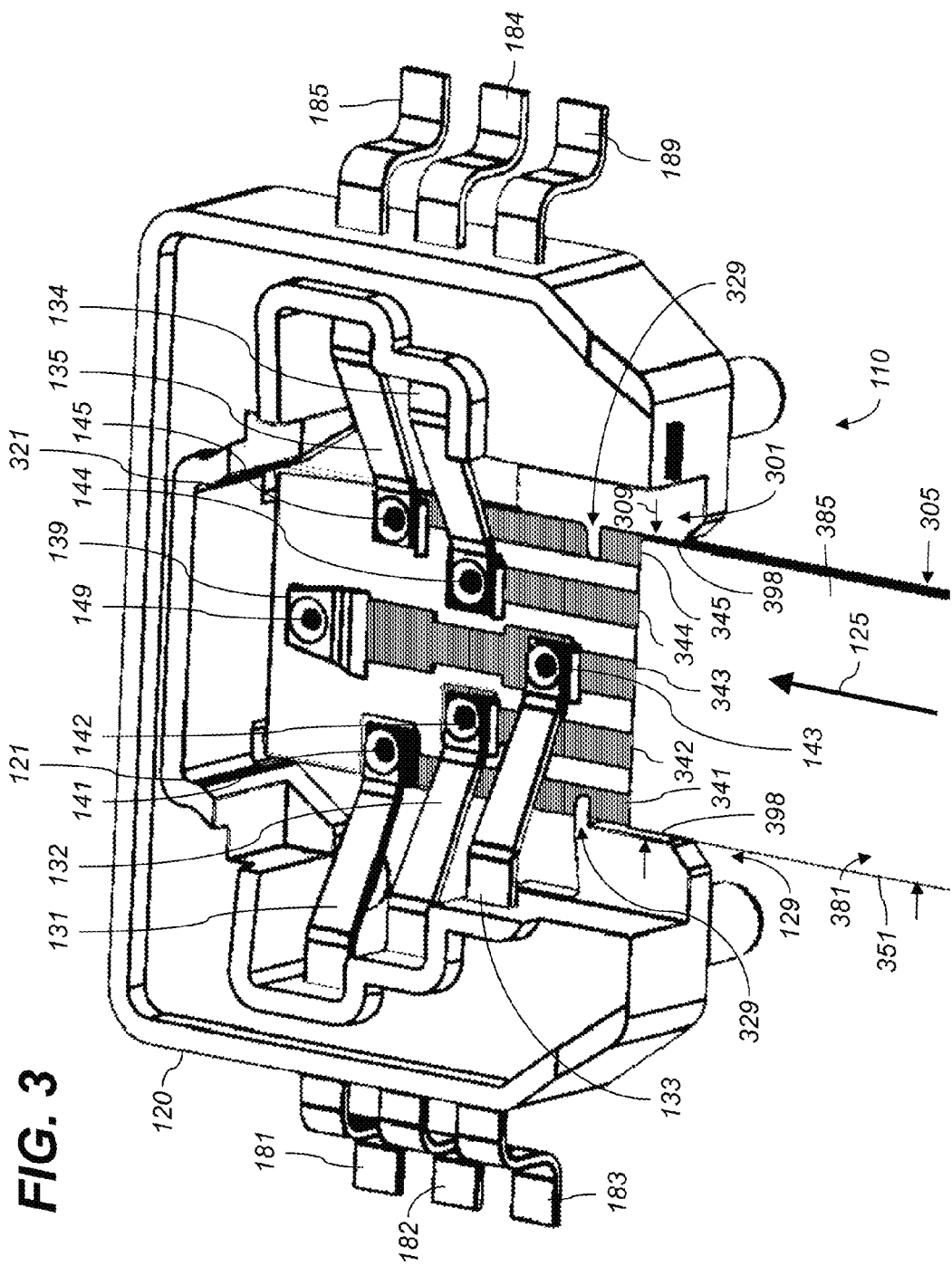
FIG. 3 is a top perspective view, a portion of which is partially cut away, of the connector of FIGS. 1 and 2, including a substrate partially inserted therein.

FIG. 1 is a perspective view of an electrical connector according to an exemplary embodiment. As discussed in greater detail herein the electrical I connector 110 is adapted to receive a first substrate 351 (FIG. 3).

Electrical connector 110 includes a housing 120. The housing 120 can be injection-molded, machine, or otherwise formed so it has sufficient mechanical strength to retain the pins 131, 132, 133, 134, 135, 139. The housing 129 has an interior cavity 138 into which the pins protrude. The interior cavity 128 is sized and shaped to receive a substrate removably inserted in the housing 120. The substrate is inserted through the port 129 in housing 120. The port 129 can be a hole, slot, slit, recess, or other access feature permitting the first substrate 351 to be releasably inserted into the interior 128 of the electrical connector 110, or otherwise brought into operative arrangement with electrical connector 110 as described herein.

The housing 120 also includes at least one first alignment feature 121, defined within the interior cavity and opposite a port side of the housing 120. Each first alignment feature 121 is spaced apart from the port 129 to define a direction 125 of permitted insertion of the first substrate 351 into the electrical connector 110. The defined direction 125 of permitted insertion can extend substantially from the port 129 toward the at least one alignment feature 121.

The electrical connector 110 includes a plurality of function pins. According to this exemplary embodiment five function pins 131, 132, 133, 134, 135 are disposed, although any number greater than two is typically preferred. The function pins 131, 132, 133, 134, 135 are mounted to housing 120, in this example by being incorporated in the plastic of housing 120 during an injection-molding process that forms the housing 120. For purposes described herein, the term "mounted to" provides for protrusion beyond the housing 120 in any direction, whether externally or internally. Each function pin 131, 132, 133, 134, 135 has a respective contact 141, 142, 143, 144, 145 arranged to electrically connect to at least a respective one of a plurality of conductive tracks (FIG. 3) of the first substrate 351 inserted in the electrical connector 110. Each contact 141, 142, 143, 144, 145 can contact the same conductive track as another contact 141, 142, 143, 144, 145, or a conductive track contacted by no other contact 141, 142, 143, 144, 145. Contacts 141, 142, 143, 144, 145 are arranged between the port 129 and the at least one first alignment feature 121 in the defined direction 125 of permitted insertion. As discussed above, the term "between" does not necessarily imply or prohibit collinearity. As discussed below, in various aspects, the function pins advantageously interrelate with substrates having various configurations of conductive tracks.

A sense pin 139 is mounted to the housing 120, the sense pin 139 having a contact 149 adapted to electrically connect to at least one of the plurality of conductive tracks of a first substrate 351 inserted a predetermined distance 352 (FIG. 3) into the electrical connector 110 and along the defined direction 125 of permitted insertion.

In various aspects, the sense pin 139 and each function pin 131, 132, 133, 134, 135 includes a plurality of electrically-connected segments (for clarity, not labeled), at least one of the segments being mechanically mounted to the housing 120. Each electrically-connected segment can be stamped, die-cut, or otherwise formed. In various aspects, the housing 120 has a port side 179 having port 129 and two pin sides 171, 172 laterally adjacent to port side 179. The sense pin 139 and various function pins 131, 132, 133, 134, 135 protrude through corresponding ones of the pin sides 171, 172. The housing 120 can also have a fourth side 174 opposite the port side 179. The fourth side 174 can be adjacent to one or both of the pin sides 171, 172. As noted, the herein-depicted connector is exemplary and therefore other suitable shapes and configurations are possible. That is, the connector 110 can have more than four sides, in which case the term "fourth" does not constrain the fourth side 174 to appear a particular place around the perimeter of the housing 120 or its footprint.

According to this exemplary embodiment, the function pins 131, 132, and 133 are mounted to the housing 120 and include segments 181, 182, 183, respectively, that protrude through the pin side 171 beyond the perimeter of housing 120 to permit making electrical contact between electrical connector 110 and a printed-circuit board (PCB) or other component to which electrical connector 110 is mounted. Each segment 181, 182, 183 is electrically connected to the respective pin 131, 132, 133 and any other segments thereof. In various aspects, mounting features 122 engage with corresponding features in a PCB (not shown) to retain electrical connector 110 in position with respect to the PCB. Function pins 134, 135, and sense pin 139, include segments 184, 185, 189, respectively, that protrude through pin side 172 beyond the perimeter of the housing 120 to likewise enable electrical contact.

As shown according to this embodiment, the contact 149 of sense pin 139 can be arranged farther from the port 129, e.g., closer to the at least one first alignment feature 121, than the respective contact 141, 142, 143, 144, 145 of at least one of the function pins 131, 132, 133, 134, 135. This can advantageously reduce the chance of false-insertion detection in systems, such as that described below with reference to FIG. 6. The contact 149 of sense pin 139 can be closer to the at least one first alignment feature 121 than each of the respective contacts 141, 142, 143, 144, 145 of function pins 131, 132, 133, 134, 135 in the defined direction 125 of permitted insertion. In this way, as a first substrate 351 (FIG. 3) is inserted into the interior of the connector 110, the sense pin contact 149 is encountered last.

Figure 2:
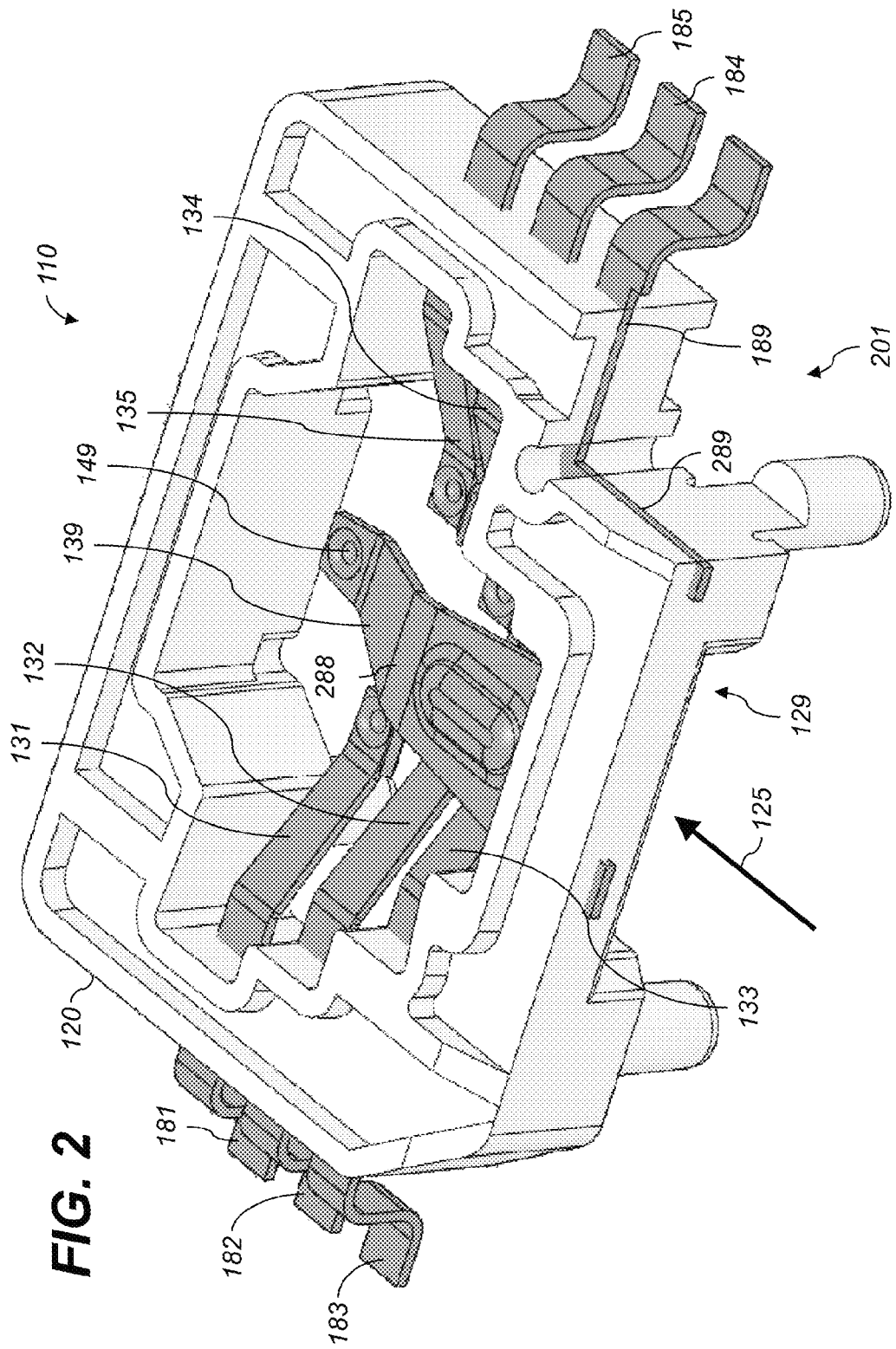
FIG. 2 is a bottom perspective view, a portion of which is partially cut away, of the connector of FIG. 1.

FIG. 2 is a partial-cutaway bottom perspective view of the connector 110, in which one corner 201 is cut away to more clearly show various electrically-connected segments 289, 189 of the sense pin 139. Electrically-connected segment 288 of sense pin 139 is also visible, connected to the sense pin contact 149.

According to this embodiment, each electrically-connected segment of the sense pin 139, e.g., segments 288, 289, 189, extends substantially parallel or substantially perpendicular to the defined direction 135 of permitted insertion of a first substrate 351 (FIG. 3). Routing the sense pin 139 in this manner substantially using a plurality of non-diagonal segments with respect to the insertion direction 135 can reduce stresses on the sense pin 139 as substrates 351 are routinely inserted and removed, extending the life of sense pin 139 and thus of the electrical connector 110. According to at least one version, at least one of the plurality of electrically-connected segments, e.g., segment 189, extends substantially perpendicular to the defined direction 125 of permitted insertion.

FIG. 3 is a partial-cutaway perspective of a first substrate 351 that is inserted in the exemplary electrical connector 110. This view has been augmented to provide needed clarity for purposes of describing various features. More specifically, a portion 301 of the housing 120 above the port 129 is cut away to more clearly show the first substrate 351 (the cut-away area extends across substrate 351 to show blocking features 329, discussed below). In addition, portions adjacent to alignment features 121, 321 are cut away to more clearly show the profile of the connector 110. Portions of sense pin 139 are also not shown in this view so that conductive track 343, contact 143, and nearby components are visible.

For purposes of this discussion, the first substrate 351 can be a substrate for a test strip, as discussed below and having a width 305. The first substrate 351 is inserted into electrical connector 110 by pushing or otherwise moving it into the port side of the connector in the defined direction 125 of permitted insertion. Moreover and according to the exemplary embodiment, the port 129 and the PCB or other surface to which the electrical connector 110 is mounted constrain the first substrate 351 (and thus test strip 550, FIG. 5, in various aspects) to lie substantially within a plane of permitted insertion.

Disposed over the first substrate 351 is a plurality of conductive tracks 341, 342, 343, 344, 345, electrically discontinuous from each other. At least one conductive track is provided, wherein a total of five (5) conductive tracks 341, 342, 343, 344, 345 are disposed over a face surface 381 of first substrate 351, and are discussed below with reference to FIGS. 7-13 based on various configurations thereof. In this figure, conductive tracks 341, 342, 343, 344, 345 are shown hatched to distinguish them from sense pin 139 and function pins 131, 132, 133, 134, 135. In the example shown, at least one insulating layer 385 is disposed over the conductive tracks 341, 342, 343, 344, 345 except for an area at one end of the first substrate 351, as shown, to permit electrical contact. As discussed herein, each function pin contact 141, 142, 143, 144, 145, 149 makes electrical contact with respective conductive tracks 341, 342, 343, 344, 345 when the first substrate 351 is fully inserted in electrical connector 110.

In various examples, the contacts 141, 142, 143, 144, 145, 149 of the function pins 131, 132, 133, 134, 135 and the sense pin 139 are vertices of a convex polygon in the plane of permitted insertion. In various examples, contact 149 of sense pin 139 is arranged so that a straight line can be drawn in the plane of permitted insertion from contact 149 to any other contact 141, 142, 143, 144, 145 without crossing a straight line between any two adjacent contacts (e.g., 141-142, 142-143, 143-144, 144-145, 145-149, 149-141). These examples permit more straightforward routing of conductive tracks 341, 342, 343, 344, 345, as discussed below.

The port 129 can include one or more blocking feature(s) 329 adapted to oppose or prevent the insertion of a second substrate (not shown) having a thickness greater than a selected thickness limit. For example, blocking features 329 can be protrusions designed to be a certain predetermined height above the PCB or other device to which electrical connector 110 is mounted. Any substrate thicker than a predetermined height will be pressed by the PCB against blocking features 329 and thus restricted or hindered from fully entering the port 129. Alternatively, blocking features 329 can such as pairs of pins or other protrusions can be provided, the features being spaced a fixed distance apart to permit only substrates with thicknesses less than or equal to the fixed distance to pass port 129.

The housing 120 can also include at least one second alignment feature 321 spaced apart from the port 129 and the at least one first alignment feature 121. The first and second alignment features 121, 321 are discussed below with reference to FIG. 5. In various examples, the housing 120 is bilaterally symmetrical, so that a first alignment feature 121 and a second alignment feature 321 are symmetrical about an axis of symmetry of the housing 120. In various other examples, the axis of symmetry is parallel to the defined direction 125 of preferred insertion.

In various aspects, the width 309 of port 129 is not more than about 1.1 times selected width 305 of a first substrate 351 ("~1.1×"), or not more than 1.05×, or not more than 1.0748×. In the exemplary embodiment, the port 129 includes two guiding surfaces 398 arranged on opposite sides of port 129 and extending substantially parallel to the defined direction 125 of permitted insertion. In various examples, width 305 is 5.5±0.15 mm and width 309 is 5.7±0.05 mm, so 5.75 mm/5.35 mm≈1.0748 is the maximum factor by which the port width 309 exceeds the width 305 of the first substrate 351.

The sense pin contact 149 can be arranged between the respective contacts of at least two of the function pins laterally, i.e., in a direction substantially perpendicular to the defined direction 125. In the example shown, the sense pin contact 149 is disposed laterally between either of function pin contacts 141 and 142, and either of pin contacts 144 and 145. The sense pin contact 149 can be collinearly aligned with laterally disposed contacts or offset therefrom and irrespective of the orientation of the segments of the sense pin 149.). That is, sense pins having diagonal segments, or including no segments in the plane of permitted insertion (e.g., sense pin 139 can be a pogo pin) can be disposed in this manner.

Figure 4:
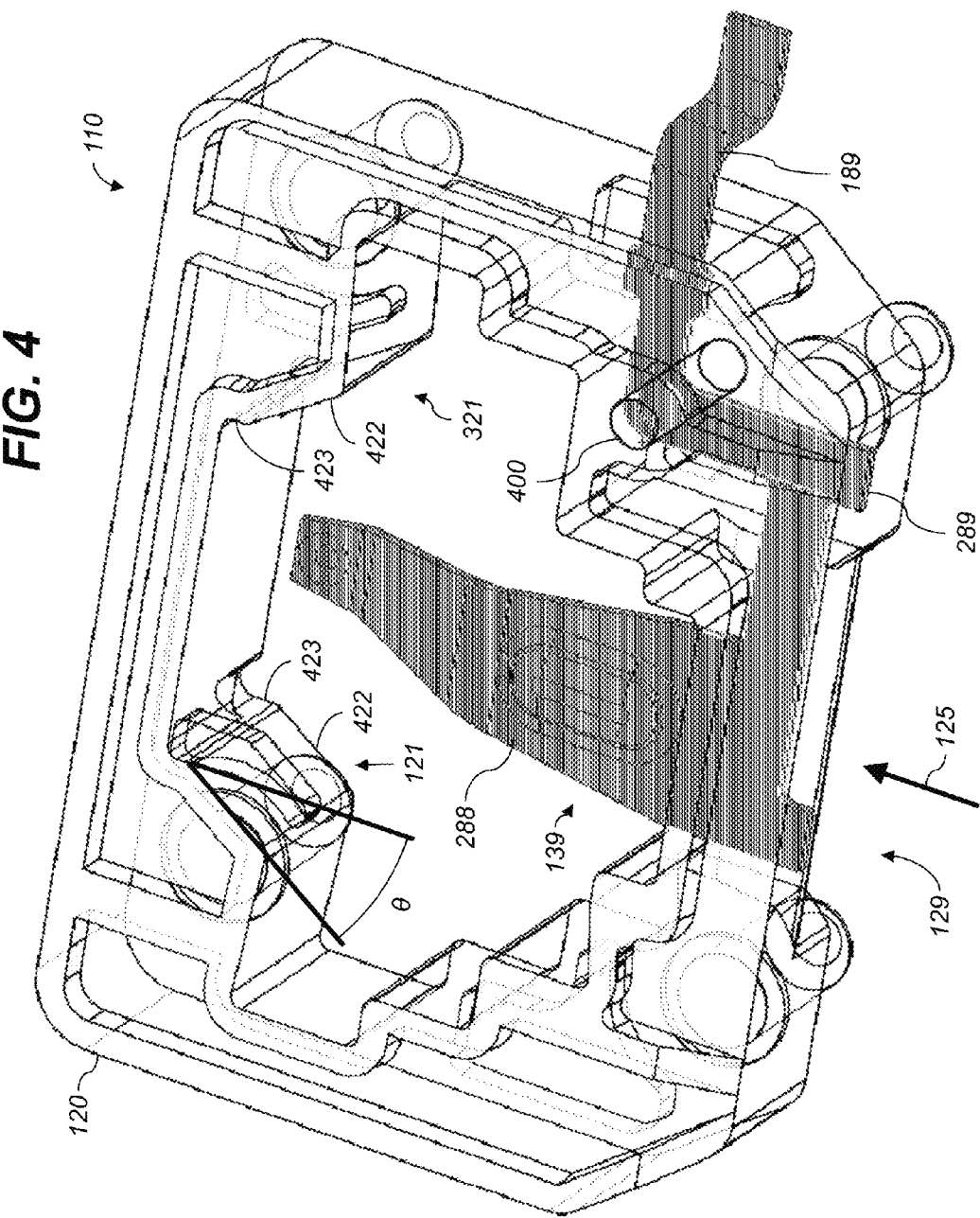
FIG. 4 is a bottom perspective view of the connector of FIGS. 1-3, partially sectioned to depict a sense pin in the connector housing in accordance with one embodiment.

FIG. 4 illustrates the prior exemplary electrical connector 110 including a sense pin in accordance with one segmented configuration. The sense pin 139 is shown hatched for clarity. As previously described and for purposes of this embodiment, the housing can be fabricated from a molding process, such as an injection molding process. The sense pin 139 is formed, then is retained in the mold (not shown) by grips (e.g., cylindrical pins) while the housing 120 is molded around the retained sense pin. Those grips leave at least one void 400 in housing 120. Function pins can also be similarly formed and molded-in, with or without retention grips. Function pins or the sense pin 139 can also be similarly retained during molding by grips holding parts of the pins outside the housing 120, e.g., segment 189.

In various examples, one or more first substrate(s) 351 are test strips used with a test meter, e.g., a glucose meter. The substrates 351 can be cycled through the connector 110, i.e., inserted and subsequently removed, four or more times per day. An embodiment of the connector 110 has a working life of at least five years, for a total of at least 7300 cycles. During each cycle, the sense pin 139 and the function pins 131, 132, 133, 134, 135 flex or bend. As the pins 131, 132, 133, 134, 135, 139 experience strain, residual stresses in the materials of those pins can initiate cracks or accelerate their propagation, possibly causing fatigue failure of one or more of the pins. Accordingly, it is useful to fabricate the connector 110 in a manner that reduces residual stresses in the pins.

When the housing 120 is injection-molded around the pins 131, 132, 133, 134, 135 (all FIG. 2), 139, one source of residual stresses is pressure applied by the molten plastic on the pins. Retaining the pins in the mold only by the segments 181, 182, 183, 184, 185 (all FIG. 2), 189 that protrude from the mold can permit the molten plastic to push the pin away from the port through which plastic enters the mold. This can cause translation or rotation of a pin in the mold, and can leave residual stresses in the pin or the plastic. In an example in which the fill port is diagonally across the housing 120 from the segment 289, diagonal segments in the pin 139 can be less resistant to the force applied by the plastic than are segments parallel or perpendicular to the defined direction 125. Such diagonal segments can be substantially parallel or perpendicular to the flow of plastic, instead of oblique thereto. Not using such diagonal segments can reduce twisting of the pin 139 during molding. Using the grips discussed above more firmly anchors the pin 139 in the mold, providing additional resistance to the force exerted by the molten plastic.

In various aspects, the sense pin 139 can be designed with no segment (e.g., segments 288, 289, 189) extending other than substantially parallel or substantially perpendicular to the defined direction 125 of permitted insertion. This orientation can improve the stability and repeatability of forces on the sense pin 139 as a first substrate 351 (FIG. 3) is inserted and removed from the connector 110, advantageously increasing the lifetime of the sense pin 139 and thus of connector 110.

The connector 110 can include at least one first alignment feature 121, as discussed above. First alignment feature(s) 121, second alignment feature(s) 321, or both, can include at least one guiding surfaces 422 and at least one retaining surface 423, disposed along the defined direction 125 of permitted insertion. Guiding surface(s) 422 form respective acute angle(s) θ (each surface 422 can have a different value of θ) with the defined direction 125 of permitted insertion. Retaining surface(s) 423 are substantially parallel to direction 125 of permitted insertion. Guiding surface(s) 422 lead a first substrate 351 (FIG. 3) as a leading edge thereof approaches retaining surface(s) 423. Retaining surface(s) 423, together with the port 129, hold the first substrate 351 in a preferred angular position with respect to the sense pin 139 and the function pins (FIG. 1).

Figure 5:
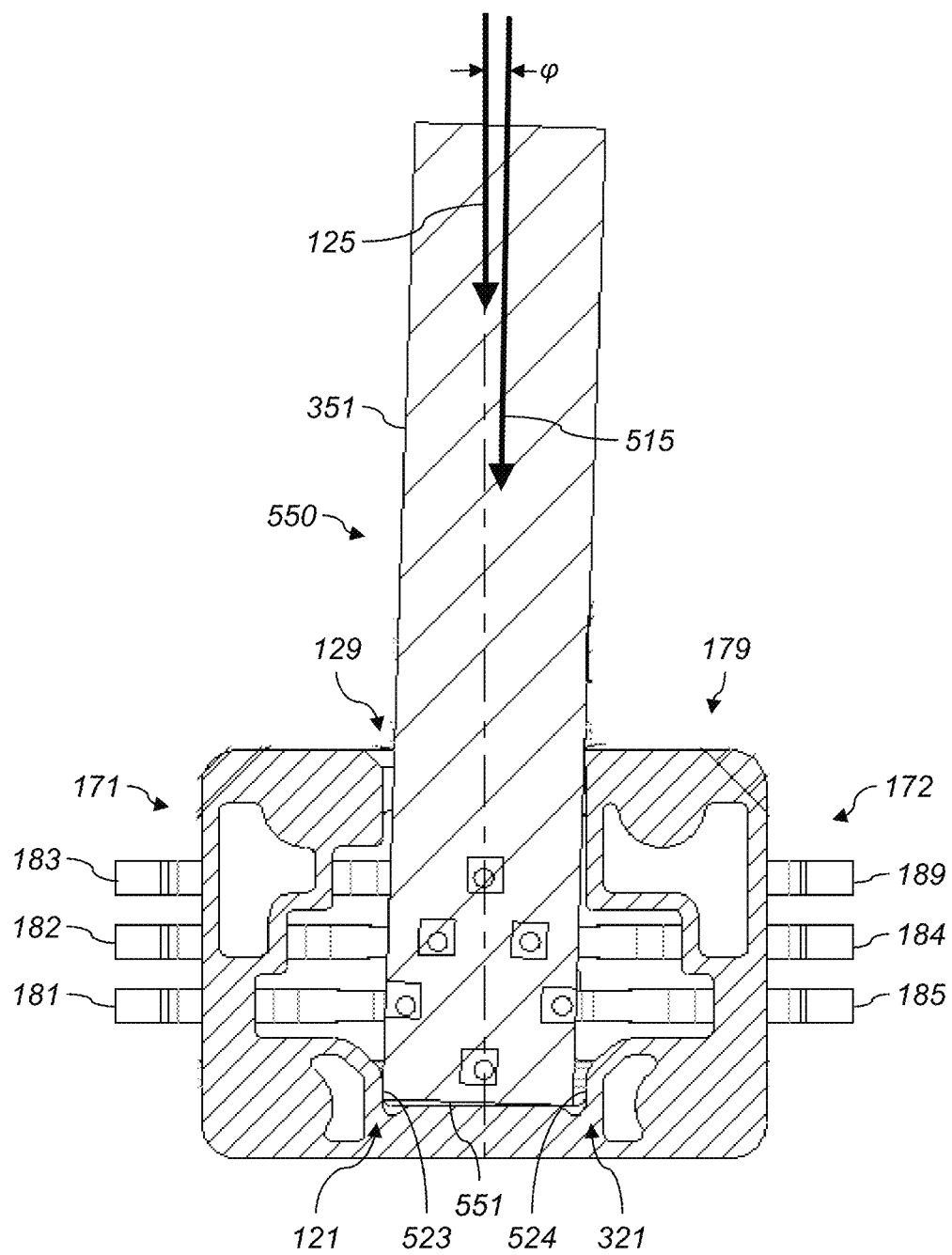
FIG. 5 is a cross-sectional view of a test strip inserted in a connector.

FIG. 5 depicts a bottom view of test strip 550 partially inserted in the electrical connector 110. The test strip 550 includes a substrate 351, as shown in FIG. 3. Retaining surfaces 523, 524 are as retaining surface 423 in FIG. 4.

In various aspects, second alignment feature 321 is spaced apart from the port 129 and first alignment feature 121. Alignment features 121, 321 are arranged to define a permitted angle φ of first substrate 351 inserted into electrical connector 110 with respect to direction 125 of permitted insertion. If longitudinal axis 515 of test strip 550 is farther in magnitude from direction 125 than permitted angle φ, test strip 550 will be blocked from full insertion into electrical connector 110 by alignment feature 121, 321, or both. In the example shown, φ is at the permitted angle of (in this example) 1.93°. Test strip 550 can only be fully inserted into electrical connector 110 if longitudinal axis 515 is within 1.93° (in this example) of direction 125. As shown, at this angle, end 551 of test strip 550 is in contact with retaining surface 523 but not with retaining surface 524. If longitudinal axis 515 were 1.93° counterclockwise from direction 125, instead of 1.93° clockwise as shown here, end 551 would be in contact with retaining surface 524 but not with retaining surface 523. The spacing between retaining surfaces 523 and 524, width 309 (FIG. 3) of port 129, and the relative positions of port 128 and alignment features 121, 321, are selected to provide a desired direction 125 and permitted angle φ based on width 305 (FIG. 3) of test strip 550 or its substrate 351.

Figure 6:
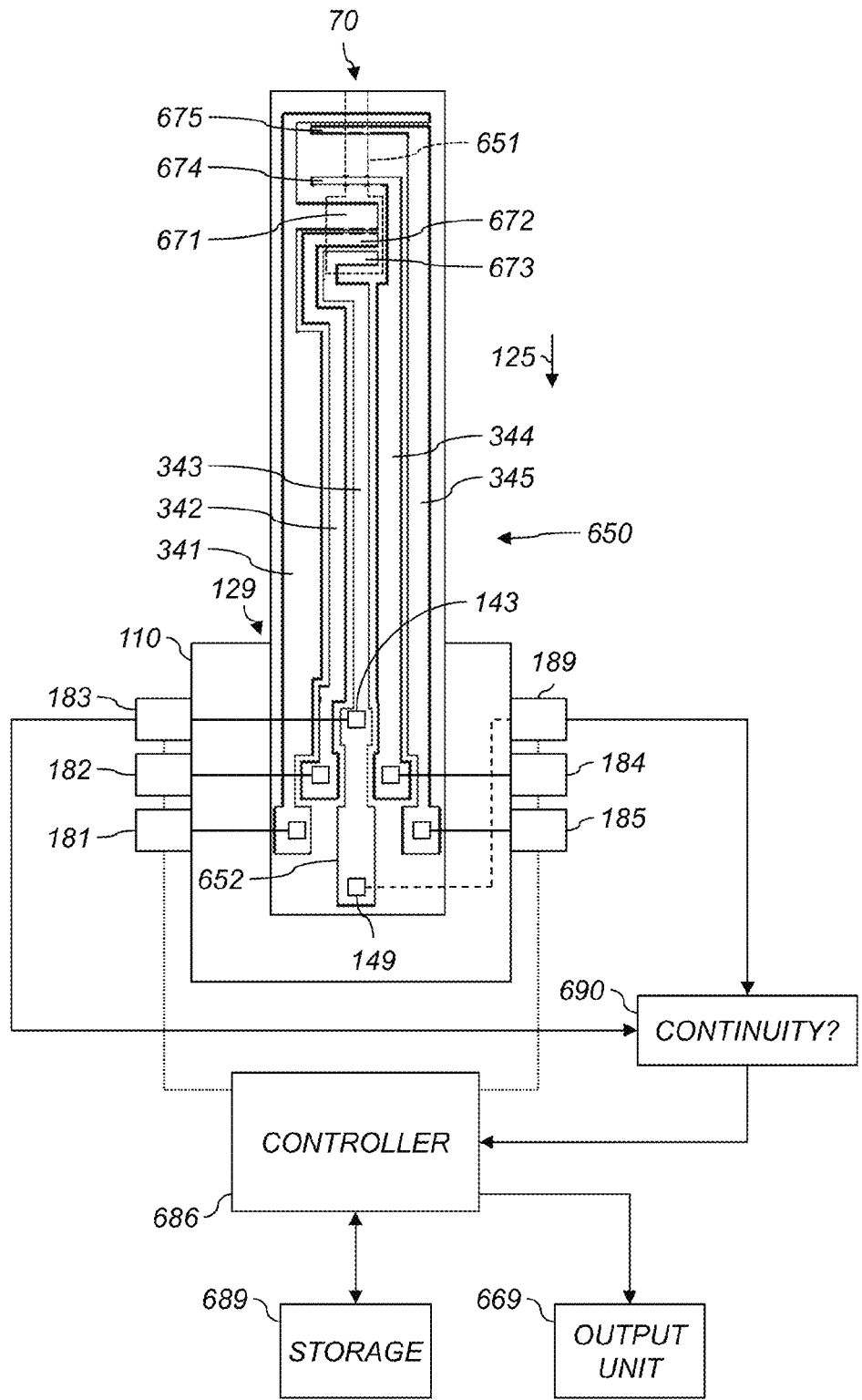
FIG. 6 is a partially diagrammatic view of a system for detecting an analyte in a bodily-fluid sample, including a connector and according to one version.

FIG. 6 shows components of a system for detecting an analyte in a bodily-fluid sample according to various aspects. As shown herein, a controller 686 controls operation of the system. Controller 686 can include a microcontroller, microprocessor, field-programmable gate array (FPGA), programmable logic array or device (PLA or PLD), programmable array logic (PAL) device, digital signal processor (DSP), or other logic or processing component adapted to perform functions described herein, or more than one of any of those, in any combination.

Test strip 650 is similar to test strip 550 and includes a sample-receiving chamber 651 (dashed outline) and a plurality of conductive tracks 341, 342, 343, 344, 345 electrically discontinuous from each other. As previously noted, at least two conductive tracks are required. Each conductive track 341, 342, 343, 344, 345 is arranged at least partially on a first side 381 (FIG. 3) of the test strip 650, and is and at least partially adjacent to the sample-receiving chamber 651. That is, each conductive track 341, 342, 343, 344, 345 is arranged so that the track's electrical properties can be influenced by a sample in the sample-receiving chamber 651, or so that electrical signals through the track can be applied to a sample in the sample-receiving chamber. As shown herein, each conductive track 341, 342, 343, 344, 345 can be adjacent to the sample-receiving chamber 651 on any side thereof, or more than one side thereof. The test strip 650 can also include other conductive tracks (not shown) that are not necessarily adjacent to the sample-receiving chamber 651. In the example shown, a fluid sample enters sample-receiving chamber 651 through port 70 (discussed below with reference to FIG. 12). Sample-receiving chamber 651 includes a sample channel extending from port 70, and an enzyme area (here, the wide rectangular portion overlapping the electrodes 671, 672, 673). An enzyme is deposited in the enzyme area; this is discussed below with reference to reagent layer 72 (FIG. 12).

Sense pin 139 (FIG. 1) is mounted to the housing 120. The sense pin contact 149 (represented as a square) is adapted to electrically connect to at least one of the respective ones of the plurality of conductive tracks 341, 342, 343, 344, 345 of the test strip 650 inserted in the electrical connector 110. As previously discussed, the sense pin contact 149 can be arranged opposite the port 129 along the defined direction 125 of permitted insertion. The sense pin contact 149 does not have to be centered laterally (i.e., in a direction substantially perpendicular to the direction 125). In various examples, each of the pin contacts can electrically connect to a respective, different conductive track 341, 342, 343, 344, 345, or more than one of the pin contacts can electrically connect to the same one of the conductive tracks 341, 342, 343, 344, 345

In the example shown, the function pins 131, 132, 133, 134, 135, 139 are not shown for clarity, but respective electrically-connected segments 181, 182, 183, 184, 185, 189 are shown, and connected to the contacts as indicated. The connection between the sense pin contact 149 and segment 189 is shown dashed only to visually differentiate that connection from other connections shown. The controller 686 can communicate with some or all of the segments 181, 182, 183, 184, 185, 189, as represented graphically by the dotted line beneath each segment 181, 182, 183, 184, 185, 189 connecting the segment to the controller 686.

A continuity sensor 690 can be adapted to detect an electrical connection between the sense pin 139 and at least one of the function pins 131, 132, 133, 134, 135, and to provide to the controller 686 an indication of which function pin(s) 131, 132, 133, 134, 135 are electrically connected to the sense pin 139. The continuity sensor 690 can be configured to detect only an electrical connection between a particular pin pair, or an electrical connection between any of a selection of pin pairs. In the example shown, a continuity sensor 690 is electrically connected to segments 183 and 189 and can thus detect an electrical connection between a function pin 133 and the sense pin 139. In the example shown, this connection is made by an electrically-conductive strap 652 when test strip 650 is substantially fully inserted into the electrical connector 110. Strap 652 electrically connects the contacts 143, 149. The continuity sensor 690 can wholly or partly be provided as a component of the controller 686, or can be a separate component communicating with the controller 686. Continuity sensor 690 can apply a test voltage or current, sense a test current, voltage, or magnetic field, or perform any suitable combination of those or other continuity-detection techniques.

As described herein, failure to detect continuity can be a result of non-insertion of a test strip 650, incomplete insertion of the test strip into the connector 110, insertion of a test strip that does not have strap 652 adapted to connect two contacts, or insertion of a test strip that does not have conductive tracks positioned to make electrical connection with the function pin and sense pin contacts 141, 142, 143, 144, 145, 149. Examples are discussed below.

A storage unit 689 stores a selected continuity configuration and a corresponding selection of two or more of the function pins. These are described below. A suitable storage unit 689 can include nonvolatile random-access memory (NVRAM), Flash memory, read-only memory (ROM), mask hardwiring, laser-trimmed resistors or traces on a silicon die, jumpers or resistors on a PCB or die, dual inline package (DIP) switches, PCB bridges or cuts, or other storage devices. The selected continuity configuration can be stored as data to be read by controller 686 or as code to be executed by controller 686. Storage unit 689 can include nonvolatile program storage for controller 686.

The controller 686 can be adapted to automatically respond to an indication from the continuity sensor 690 that an electrical connection has been detected between the sense pin 139 and at least one of the function pins 131, 132, 133, 134, 135. Controller 686 compares the provided indication of which of the function pins 131, 132, 133, 134, 135 is or are connected to sense pin 139 to the stored selected continuity configuration from storage unit 689. If the provided indication corresponds to the stored selected continuity configuration, controller 686 takes a measurement. As described herein, the terms "corresponds to" means that the provided indication and the selected continuity configuration represent the same conductive track on the test strip, whether or not the same identifier is used in the indication and the configuration. In an example shown here, a storage unit 689 can store a continuity configuration of "pin 133 connected" to the sense pin 139, and a corresponding selection of "pins 131, 132".

The controller 686 can take a measurement by activating those function pin(s) indicated by the stored corresponding selection from the storage unit 689 (e.g., activate pins 131, 132). Activating those function pins results in applying a test electrical signal to or across the sample-receiving chamber 651 (note that the term "across" is conventional in the electrical arts and does not constrain the mechanical orientation of electrodes such as electrodes 671, 672). A resulting electrical signal can be measured to detect the analyte in the sample-receiving chamber 651. According to one version, the electrical signal is a voltage and the controller 686 is further adapted to measure a current between the two of the conductive tracks to detect the analyte.

"Detecting the analyte" can include detecting whether or not an analyte is present in the sample-receiving chamber and, if so, detecting a property of that analyte. Continuing the example above, when the controller 686 receives from continuity sensor 690 an indication that a function pin 133 is electrically connected to the sense pin 139, controller 686 sees a match with the stored continuity configuration and retrieves the corresponding selection from storage unit 689. Since the corresponding selection includes function pins 131 and 132, controller 686 can activate the function pins 131, 132 by supplying voltage or current to the segments 181, 182, respectively.

The controller 686 can be further adapted to present an error indication if the provided indication does not correspond to the stored selected continuity configuration. The controller 686 can present the error via an output unit 669. Output unit 669 can include a device that produces a visual or audible indication to the user. For example the output unit 669 can include at least one light that blinks or is otherwise illuminated when the controller 686 presents the error; a bell, beeper or buzzer that sounds; or a horn that blows. According to other aspects, an audio- or visual-reproduction system can be activated (e.g., a computer screen that displays a pop-up error dialog), or a network interface that transmits information about the error to a human-machine interface (HMI), server, terminal, smartphone, pager, or other computing or communications device.

In other aspects, a storage unit 689 can store a plurality of selected continuity configurations and respective corresponding selections of two or more of the function pins. For example, a storage unit 689 can store:

| Continuity configuration: pin(s) connected to sense pin 139 | Selection of function pins |
| --- | --- |
| 131 | 132, 131 |
| 132 | 132, 131 |
| 133 | 132, 131 |
| 134 | 135, 134 |
| 135 | 135, 134 |

In regard to these aspects, the controller can compare the provided indication to each of the stored selected continuity configurations. If the provided indication corresponds to one of the stored selected continuity configurations, the controller 686 activates the ones of the function pins indicated by the stored respective corresponding selection. An electrical signal is thus applied across the sample-receiving chamber 651 to detect the analyte in sample-receiving chamber 651, as described above.

In various aspects, more than one set of function pins can be used simultaneously. The stored corresponding selection specifies that at least as many as two sets of at least two of the function pins each be activated. In an example, storage unit 689 stores:

| Continuity configuration: pin(s) connected to sense pin | Selection of function pins: first set | Selection of function pins: second set |
| --- | --- | --- |
| 131 | 132, 131 | 135, 134 |
| 132 | 132, 131 | 135, 134 |
| 133 | 132, 131 | 135, 134 |
| 134 | 134, 135 | 131, 132 |
| 135 | 134, 135 | 131, 132 |

In various of these aspects, the bodily-fluid sample is whole blood. The controller can be adapted to apply the test electrical signal by applying a glucose-measurement signal across the function pins in the first set and, simultaneously or sequentially (in either order) applying a hematocrit-measurement signal across the function pins in the second set. This permits correcting for noise in glucose measurements that can be caused by varying hematocrit levels.

In various aspects, the first set can include three function pins of the connector 110. In an example, the storage unit 689 stores the following, and the row marked (*) corresponds to the example shown in FIG. 6:

| Continuity configuration: pin(s) connected to sense pin | Selection of function pins: first set | Selection of function pins: second set |
| --- | --- | --- |
| 131 | 132, 133; 131 | 135, 134 |
| 132 | 132, 133; 131 | 135, 134 |
| 133 (*) | 132, 133; 131 | 135, 134 |
| 134 | 134, 133; 135 | 131, 132 |
| 135 | 134, 133; 135 | 131, 132 |

The controller 686 applies the glucose measurement signal between a first of the three of the function pins and a second of the three of the function pins, e.g., in row (*), between pins 132 and 131. The controller 686 also applies the glucose measurement signal between a third of the three of the function pins and the second of the three of the function pins, e.g., between pins 133 and 131. For example, pins 132 and 133 can be electrically connected, e.g., via conductive tracks 342, 343, respectively, to respective working electrodes 672, 673, both of which are operationally arranged adjacent to sample-receiving chamber 651 with respect to a common counter/reference electrode 671 electrically connected via conductive track 341 to pin 131. This provides a simple failsafe wherein measurements can be taken using only pin 132 if the electrode 673 or the conductive track 343 connected to pin 133 is inoperative (e.g., open due to mechanical damage), and vice versa. In various aspects, this failsafe is used and hematocrit measurement is not used.

In various examples, hematocrit can be measured with pins 134, 135 in the second set. These pins are connected via the conductive tracks 344, 345, respectively, to electrodes 674, 675, respectively. The electrodes 674, 675 are positioned between the port 70 and the electrode 671, which is the closest of electrodes 671, 672, 673 to port 70. The controller 686 applies a hematocrit-measurement signal or another sample-parameter measurement signal to the electrodes 674, 675. The controller 686 measures resulting electrical characteristics (e.g., voltage, current, waveform, or frequency) of signals on the electrodes 674, 675 and uses the measured characteristics to determine a parameter of the sample in the sample-receiving chamber 651. For example, the controller 686 can use a hematocrit measurement to set a glucose-assay delay time. Controller 686 then waits for the glucose-assay delay time to pass before applying the glucose measurement signal to the selected function pins.

Measuring hematocrit can permit more accurate glucose readings in blood samples having a high hematocrit level or low hematocrit level. A hematocrit level represents a percentage of the volume occupied by red blood cells. In general, a high hematocrit blood sample is more viscous (up to about 10 centipoise at 70% hematocrit) than a low hematocrit blood sample (about 3 centipoise at 20% hematocrit). In addition, a high hematocrit blood sample has a higher oxygen content than a low hematocrit blood because of the concomitant increase in hemoglobin, which is a carrier for oxygen. Thus, the hematocrit level can influence the viscosity and oxygen content of blood. Both viscosity and oxygen content can change the magnitude of the glucose current and in turn cause the glucose concentration measurement to be inaccurate. Measuring hematocrit permits correcting for those inaccuracies. Examples of hematocrit correction are given in US Patent Application Publication No. 2011/0005941, incorporated herein by reference.

An electrical connector 110 can further include two or more alignment features arranged, e.g., as shown in FIG. 3. Respective contacts 141, 142, 143, 144, 145, 149 (FIG. 3) of function pins 131, 132, 133, 134, 135 and sense pin 139 are between port 129 and each of the alignment features 121, 321 (both FIG. 3) in direction 125 of permitted insertion.

In various aspects, as shown in FIG. 4, sense pin 129 includes a plurality of electrically-connected segments, e.g., segments 288, 289, 189. At least one of the segments is mechanically mounted to housing 120. Each segment extends substantially parallel or substantially perpendicular to direction 125 of permitted insertion. In various aspects, sense pin 129 does not include any segment extending other than substantially parallel or substantially perpendicular to direction 125 of permitted insertion.

As discussed above, failure to detect continuity on insertion of a test strip can be a result of insertion of a test strip that does not have strap 652 adapted to connect two contacts. Detection failure can also be a result of insertion of a test strip having strap 652 positioned in a way other than that indicated by the stored continuity configuration. Accordingly, various aspects of analytical test strip and test meter combinations advantageously permit readily identifying analytical test strips as suitable or unsuitable for use by the test meter based on whether the signal processing module senses an appropriate electrical continuity or electrical discontinuity. Such identification advantageously permits the test meter to proceed with analyte determination only when appropriate, thus avoiding potentially improper, erroneous or inaccurate analyte determinations based on the use of unsuitable analytical test strips.

It is envisioned that various commercial markets can be supplied with analytical test strip and meter combinations according to various aspects. For example, commercial market "A" can be supplied with analytical test strips that have a first electrical configuration (e.g., strap 652 connecting pins 141, 149), while commercial market "B" can be supplied with analytical test strips that have a second, different electrical configuration (e.g., strap 652 connecting pins 145, 149). In such a scenario, signal processing modules of test meters supplied to users in markets "A" and "B" would be programmed to identify analyte test strips with the appropriate electrical continuity or discontinuity as suitable for use and analyte test strips with inappropriate electrical continuity or discontinuity as unsuitable for use. If an analytical test strip configured for market A were to be inadvertently employed in market B, a market B test meter would determine that the analytical test strip was unsuitable for use (because the indication would not match the stored continuity configuration) and, if desired, display an appropriate message to a user on a display module of the test meter.

FIGS. 7-11 show layouts of conductive tracks on substrates 351 according to various aspects. A plurality of conductive tracks 341, 342, 343, 344, 345 are shown, electrically connected to contacts 141, 142, 143, 144, 145 (represented graphically as circles), respectively. The sense pin contact 149 (represented graphically as a circle in FIG. 1) is also shown. FIG. 7 shows a strap 652 electrically connecting a function pin contact 143 to the sense pin contact 149. FIG. 8 shows strap 652 electrically connecting contact 141 to contact 149. FIG. 9 shows strap 652 electrically connecting contact 142 to contact 149. FIG. 10 shows strap 652 electrically connecting contact 144 to contact 149. FIG. 11 shows strap 652 electrically connecting contact 145 to contact 149.

FIG. 12 is an exploded perspective view of an exemplary test strip. Further details are provided in US Patent Application Publication No. 2007/0074977, incorporated herein by reference.

The test strip 62 includes a first support layer 66, a spacer 60, and a second support layer 64. Support layers 66, 64 and spacer 60 can be electrically insulating, e.g., plastic. Support layers 66, 64 and spacer 60 can be sufficiently rigid to provide mechanical support to test strip 62, or can be layers coated over other sufficiently rigid structures. When fully assembled, the test strip 62 includes a sample-receiving chamber 61 for receiving a sample, e.g., a bodily-fluid sample. Sample-receiving chamber 61 is formed by a cutout area 68 in the spacer 60. A sample, e.g., a bodily-fluid sample can be delivered through a port 70. Test strip 62 can have one or two ports 70, or more. One of the ports 70 can provide a sample inlet and the other can act as a vent.

The sample-receiving chamber 61 can be adapted for analyzing small volume samples. For example, a sample-receiving chamber 61 can have a volume ranging from about 0.1 microliters to about 5 microliters, or 0.2 to about 3 microliters, or about 0.3 microliters to about 1 microliter. To accommodate a small sample volume, electrodes of the test strip can be closely spaced. For example, where spacer 60 defines the distance between electrode 1201 and electrode 1202, the height of spacer 60 can be in the range of about 1 micron to about 500 microns, or between about 10 microns and about 400 microns, or between about 40 microns and about 200 microns. More details of exemplary test strips are given in U.S. Pat. No. 8,163,162, incorporated herein by reference.

One or more electrical conductors can be disposed over support layers 64, 66. In the example shown, electrode 1201 is disposed over support layer 66 adjacent to sample-receiving chamber 61. Electrodes can be arranged spaced apart in a facing or opposing faced arrangement, or in other coplanar or non-coplanar configurations.

A reagent layer 72 can be disposed within the sample-receiving chamber 61 using a process such as slot coating, coating by dispensing liquid from the end of a tube, ink jetting, and screen printing. Such processes are described, for example, in U.S. Pat. Nos. 6,749,887; 6,689,411; 6,676,995;

and 6,830,934, each of which are hereby incorporated by reference in their entirety. In various aspects, reagent layer 72 is deposited onto an electrode and includes at least a mediator and an enzyme. A mediator can be in either of two redox states which may be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation for reagent layer 72 is described in U.S. application. Ser. No. 10/242,951, entitled, Method for Manufacturing a Sterilized and Calibrated Biosensor-Based Medical Device, published as U.S. Application Publication No. 2004/0120848, which is hereby incorporated by reference in its entirety.

Electrodes can be disposed over the face of first support layer 66 visible in FIG. 12, and over the face of second support layer 64 not visible in FIG. 12. Electrodes can be disposed on both faces of sample-receiving chamber 61, or around the edges thereof. Also disposed over support layer 66 or support layer 64 are one or more conductive tracks connected to the electrodes. In this example, conductive tracks 341, 342, 343, 344, 345 are disposed over support layer 66 and electrically connected to contacts 141, 142, 143, 144, 145 (represented graphically as black circles), respectively. A conductive track 341 is connected to the electrode 1201. Other electrodes are not shown, but each conductive track 341, 342, 343, 344, 345 can connect to zero or more electrodes. Spacer 60 can include electrically-conductive vias to provide electrical connections between conductive tracks on support layer 66 and conductive tracks on support layer 64. As discussed above with reference to FIG. 6, contacts 141, 142, 143, 144, 145, 149 electrically connect with conductive tracks 341, 342, 343, 344, 345 to permit applying electrical signals to sample-receiving chamber 61 or a fluid or bodily-fluid sample therein. Test strip 62 can include a variety of electrical contact configurations for electrically connecting to a meter. For example, U.S. Pat. No. 6,379,513 discloses electrochemical cell connection means, and is hereby incorporated by reference in its entirety.

The electrodes, e.g., electrode 1201, can be thin films. In various aspects, electrodes include conductive material formed from materials such as gold, palladium, carbon, silver, platinum, tin oxide, iridium, indium, and combinations thereof (e.g., indium-doped tin oxide or "ITO"). Electrodes can be formed by disposing a conductive material onto a support layer 66, 64 by a sputtering, electroless plating, or a screen printing process. In an example, sputtered gold electrode 1202 is disposed over side 1265 (the side not visible in FIG. 12) of support layer 64 and sputtered palladium electrode 1201 is disposed over side 1266 (the side visible in FIG. 12) of support layer 66. Suitable materials that can be employed as the insulating sheet include, for example, plastics (e.g. PET, PETG, polyimide, polycarbonate, polystyrene), silicon, ceramic, glass, and combinations thereof. For example, support layers 64, 66 can be formed from 7 mil polyester substrate(s).

In an example, support layer 66 includes a polyester base on which has been deposited, e.g., by sputtering, a Pd coating forming working electrode 1201. Dry reagent layer 72 includes buffer, mediator, and enzyme, as described herein. Spacer 60 is a double-sided adhesive having cutout area 68 that defines the electrochemical cell. The spacer can be less than about 200 µm thick. Support layer 64 includes a polyester base on which has been deposited, e.g., by sputtering, an Au coating forming reference electrode 1202. In this example, a glucose oxidase/ferricyanide system is used to determine glucose concentrations via the following reactions:

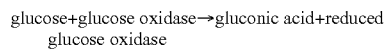

Reaction 1:
glucose+glucose oxidase→gluconic acid+reduced glucose oxidase

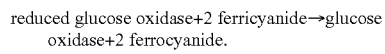

Reaction 2:
reduced glucose oxidase+2 ferricyanide→glucose oxidase+2 ferrocyanide.

Ferricyanide ($[Fe(CN)_6]^{3-}$) is the mediator, which returns the reduced glucose oxidase to its catalytic state. Glucose oxidase, an enzyme catalyst, will continue to oxidize glucose so long as excess mediator is present. Ferrocyanide ($[Fe(CN)_6]^{4-}$) is the product of the total reaction. Ideally, there is no ferrocyanide initially, although in practice there is often a small quantity. After the reaction is complete, the concentration of ferrocyanide (measured electrochemically) indicates the initial concentration of glucose. The total reaction is the sum of reactions 1 and 2.

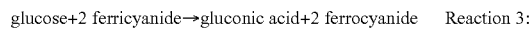

Reaction 3: glucose+2 ferricyanide→gluconic acid+2 ferrocyanide

"Glucose" refers specifically to β-D-glucose. Details of this system are described in PCT Application No. WO 97/18465 and U.S. Pat. No. 6,444,115, each of which is incorporated herein by reference.

Figure 13:
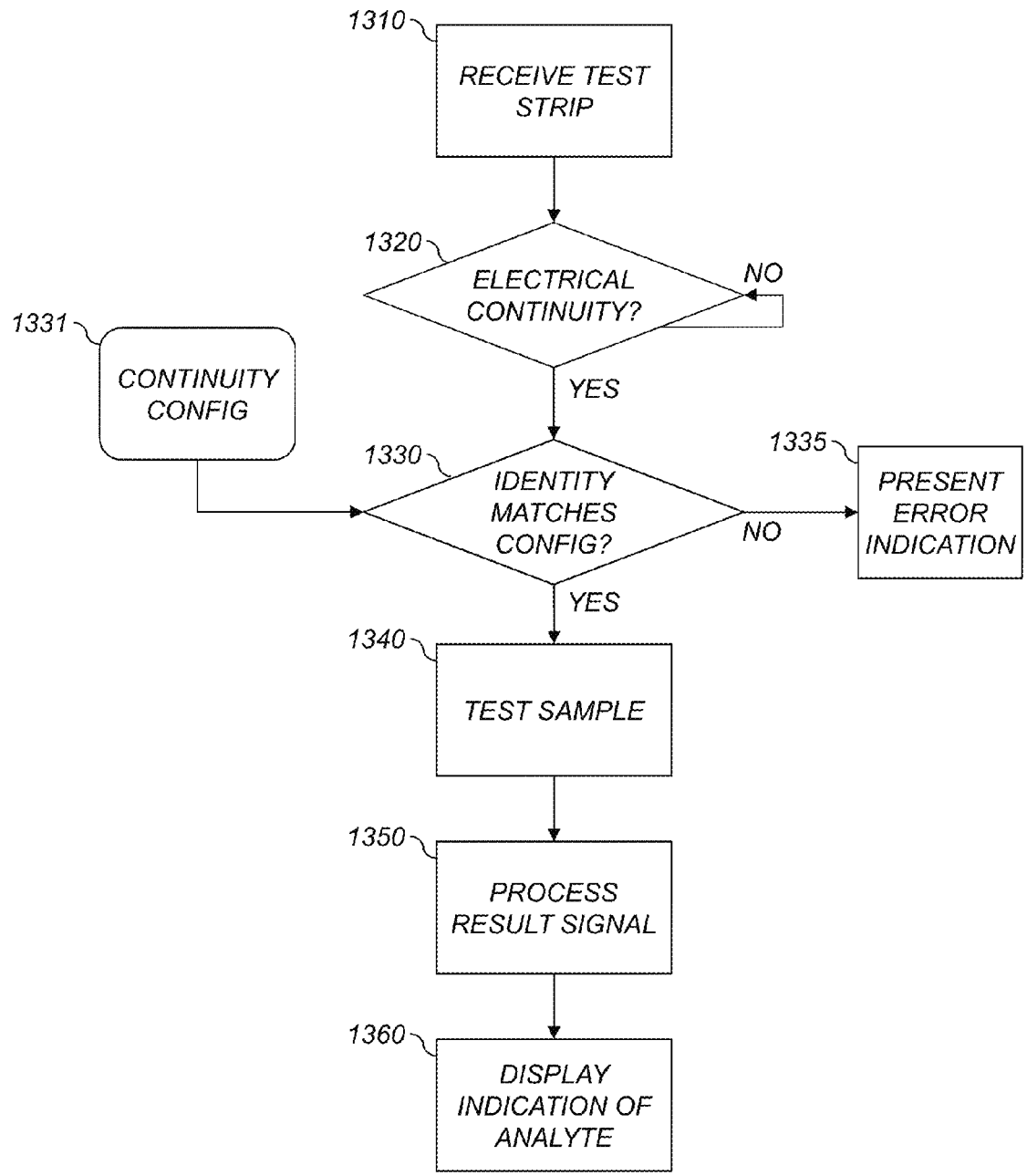
FIG. 13 is a flowchart illustrating an exemplary method for determining an analyte in a bodily-fluid sample.

FIG. 13 is an exemplary flowchart for determining an analyte in a bodily-fluid sample according to various aspects. Various combinations and orders of these steps can be used. Processing begins with step 1310.

In step 1310, an analytical test strip is received using an electrical connector of a test meter. The analytical test strip includes a sample-receiving chamber adapted to receive the bodily-fluid sample, e.g., as shown in FIG. 12. The receiving step is carried out according to this exemplary method such that at least three conductive tracks exposed on a first side of the analytical test strip make electrical contact with respective function pins of the electrical connector and at least one of the conductive tracks further makes electrical contact with a sense pin of the electrical connector, e.g., as shown in FIG. 6. Step 1310 is followed by step 1320.

In step 1320, a controller of the test meter is used to sense electrical continuity between the sense pin and a first one of the function pins. As discussed above with reference to FIG. 6, the controller can include or be electrically connected to a continuity sensor. The controller senses electrical continuity whether or not it relies on other components in doing so. When continuity is sensed, step 1320 is followed by step 1330. If no continuity is detected, the controller can wait for continuity, prompt a user to insert a strip, or signal an error.

In step 1330, when continuity is sensed, the controller compares an identity of the first one of the function pins to stored continuity-configuration information 1331. The identity of the first one of the function pins can be a pin number or position, or another identifying value correlated with those. For example, step 1320 can include a continuity sensor providing a multi-bit digital value or bitmask to the controller, that value or bitmask indicating which of the function pins is electrically connected to the sense pin. When the identity matches, step 1330 is followed by step 1340. When the identity does not match, step 1330 can be followed by step 1335.

In step 1335, the controller automatically presents an error indication. The error indicates that the identity of the first one of the function pins does not correspond to the stored continuity-configuration information. The error can be presented on a display, audio interface, network interface, or other device, e.g., as described above with reference to output unit 669 (FIG. 6).

In step 1340, if the identity of the first one of the function pins corresponds to the stored continuity-configuration information, the controller automatically applies a selected electrical signal to selected ones of the function pins indicated by the stored continuity-configuration information and measures at least one result electrical signal. Step 1340 is followed by step 1350.

In various aspects, step 1330 includes the controller automatically comparing the identity of the first one of the function pins to each of a plurality of stored values of continuity-configuration information. If the identity matches one of the plurality, step 1340 includes the controller automatically applying a selected electrical signal to selected ones of the function pins indicated by the matching stored values of the continuity-configuration information. This permits using different configurations of test strips with one controller.

In step 1350, the controller automatically processes the result electrical signal to detect whether a bodily-fluid sample has been applied to the sample-receiving chamber and, if so, to determine the analyte in the applied bodily-fluid sample. Examples are discussed below. Step 1350 can be followed by step 1360. In various aspects, the analyte is glucose and the bodily-fluid sample is a whole blood sample.

In step 1360, an indication of the determined analyte is presented on a display, e.g., by the controller automatically commanding the display. For example, the level of glucose in a blood sample, measured in mg/dL or mmol/L, can be displayed as a number.

An electrochemical (amperometric) method for measuring an analyte concentration in an aqueous sample, e.g., a bodily-fluid sample, involves placing the sample into a reaction zone (e.g., sample-receiving chamber 61, FIG. 12) in an electrochemical cell that has two electrodes (e.g., electrodes 1201, 1202, FIG. 12) having an impedance that is suitable for the amperometric measurement. The analyte is allowed to react directly with an electrode or with a redox reagent, as described above, to form an oxidizable (or reducible) substance in an amount that corresponds to the analyte concentration. The quantity of oxidizable (or reducible) substance is then determined electrochemically. Various aspects accurately determine the point in time at which the sample is detected in the reaction zone. This permits an electrochemical waveform (e.g., voltage) to be applied immediately after the sample has been applied and accurately defines an incubation period or reaction time. In turn, this improves the accuracy and precision of the assay.

First, a small, constant current source can be applied across the electrode of an electrochemical diagnostic strip and a potential difference between the electrodes is monitored. Before the sample is applied to sample-receiving chamber 61, there is a dry gap between electrodes 1201, 1202. Therefore, negligible current flows. When a sample is applied to the strip and fills the gap, the measured voltage decreases rapidly, causing the test time to be initiated. The controller 686 (FIG. 6) can be configured to recognize the decrease in voltage as indicative of a sample and automatically stops applying a constant-current electrical signal to the selected ones of the function pins 131, 132, 133, 134, 135 (FIG. 1). The controller can then apply a constant-voltage electrical signal to the selected ones of the function pins 131, 132, 133, 134, 135. While the constant voltage is applied, current or charge are measured as a function of time to permit the analyte concentration to be calculated.

The current that is measured at a predetermined time after the constant voltage is applied is a measure of the analyte concentration, once the system has been calibrated using samples having known analyte concentrations. The duration of the predetermined time is not critical. It can be at least about 3 seconds when the fluid is blood and the analyte is glucose. That duration generally provides sufficient time to dissolve reagents and reduce an amount of mediator that is readily measurable. All things being equal, at high hematocrit, longer times are needed. The duration can be <10 s. The same predetermined time can be used for multiple successive measurements of respective samples. Further examples are given in U.S. Pat. No. 6,193,873 and US Patent Application Publication No. 2007/0074977, each of which is incorporated herein by reference.

Figure 14:
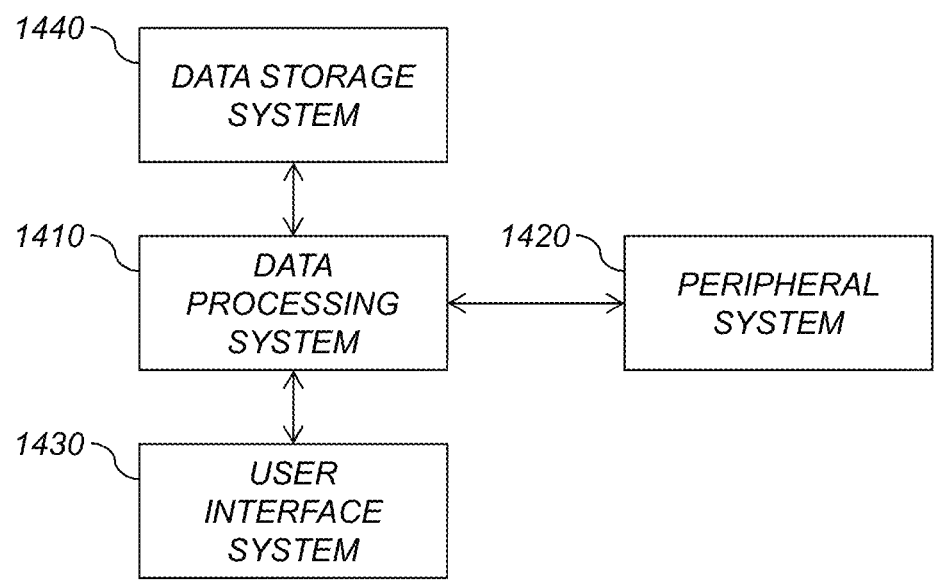
FIG. 14 is a block diagram showing components of a data-processing system useful with a controller according to an exemplary embodiment.

FIG. 14 is a block diagram showing components of a data-processing system for analyzing data and performing other analyses described herein. The system includes a data processing system 1410, a peripheral system 1420, a user interface system 1430, and a data storage system 1440. The peripheral system 1420, the user interface system 1430 and the data storage system 1440 are communicatively connected to the data processing system 1410. The controller 186 and receiver 130 can each include one or more of systems 1410, 1420, 1430, 1440.

The data processing system 1410 includes one or more data processing devices that implement the processes of the various aspects, including the example processes described herein. The phrases "data processing device" or "data processor" are intended to include any data processing device, such as a central processing unit ("CPU"), a desktop computer, a laptop computer, a mainframe computer, a personal digital assistant, a Blackberry™, a digital camera, cellular phone, or any other device for processing data, managing data, or handling data, whether implemented with electrical, magnetic, optical, biological components, or otherwise.

The data storage system 1440 includes one or more processor-accessible memories configured to store information, including the information needed to execute the processes of the various aspects, including the example processes described herein. The data storage system 1440 can be a distributed processor-accessible memory system including multiple processor-accessible memories communicatively connected to the data processing system 1410 via a plurality of computers or devices. On the other hand, the data storage system 1440 need not be a distributed processor-accessible memory system and, consequently, can include one or more processor-accessible memories located within a single data processor or device. In various aspects, data storage system 1440 in controller 686 (FIG. 6) includes code or other commands to cause signal processing module 386 to carry out a suitable algorithm that determines an analyte based on the electrochemical response of analytical test strip 650 (FIG. 6). The algorithm can accommodate the electrochemical response of various electrodes (e.g., electrode 1201, FIG. 12) within electrochemical-based analytical test strip 650.

The phrase "processor-accessible memory" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs.

The phrase "communicatively connected" is intended to include any type of connection, whether wired or wireless, between devices, data processors, or programs in which data can be communicated. The phrase "communicatively connected" is intended to include a connection between devices or programs within a single data processor, a connection between devices or programs located in different data processors, and a connection between devices not located in data processors. In this regard, although the data storage system 1440 is shown separately from the data processing system 1410, one skilled in the art will appreciate that the data storage system 1440 can be stored completely or partially within the data processing system 1410. Further in this regard, although the peripheral system 1420 and the user interface system 1430 are shown separately from the data processing system 1410, one skilled in the art will appreciate that one or both of such systems can be stored completely or partially within the data processing system 1410.

The peripheral system 1420 can include one or more devices configured to provide digital content records to the data processing system 1410. For example, the peripheral system 1420 can include digital still cameras, digital video cameras, cellular phones, or other data processors. The data processing system 1410, upon receipt of digital content records from a device in the peripheral system 1420, can store such digital content records in the data storage system 1440.

The user interface system 1430 can include a mouse, a keyboard, another computer, or any device or combination of devices from which data is input to the data processing system 1410. In this regard, although the peripheral system 1420 is shown separately from the user interface system 1430, the peripheral system 1420 can be included as part of the user interface system 1430.

The user interface system 1430 also can include a display device, a processor-accessible memory, or any device or combination of devices to which data is output by the data processing system 1410. In this regard, if the user interface system 1430 includes a processor-accessible memory, such memory can be part of the data storage system 1440 even though the user interface system 1430 and the data storage system 1440 are shown separately in FIG. 14.

Aspects of the present invention can be embodied as a system, method, or computer program product. Accordingly, aspects may take the form of entirely hardware, entirely software (including firmware, resident software, micro-code, etc.), or a combination of software and hardware. These forms and aspects can all generally be referred to herein as a "service," "circuit," "circuitry," "module," or "system."

Various aspects may take the form of a computer program product embodied in one or more computer readable medium(s) having computer readable program code embodied thereon. A computer program product can include one or more storage media, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice various aspects. Other examples of computer-readable storage media include a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. A computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, or any suitable combination of appropriate media.

Computer program code for carrying out operations for various aspects can execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions can be stored in a computer readable medium that can direct a computer, other programmable data processing apparatus, or other devices to function in a particular manner. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

PARTS LIST FOR FIGS. 1-14

60 spacer
61 sample-receiving chamber
62 test strip
64, 66 support layer
68 cutout area
70 port
72 reagent layer
110 electrical connector
120 housing
121 alignment feature
122 mounting feature
125 direction
128 interior
129 port
131, 132, 133, 134, 135 function pin
139 sense pin
141, 142, 143, 144, 145 contact
149 contact
171, 172 pin side
174 fourth side
179 port side
181, 182, 183, 184, 185 segment
189 segment
288, 289 segment
301 portion cut away
305 width
309 width
321 alignment feature
329 blocking feature
341, 342, 343, 344, 345 conductive track
351 substrate
381 face surface
385 insulating layer
398 guiding surface
400 void
422 guiding surface
423 retaining surface
515 direction
523, 524 retaining surface
550 test strip
551 end 650 test strip
651 sample-receiving chamber
652 strap
669 output unit
671, 672, 673, 674, 675 electrode
686 controller
689 storage unit
690 continuity sensor
1201, 1202 electrode
1265, 1266 side
1310 receive test strip step
1320 electrical continuity present decision step
1330 identity matches configuration decision step
1331 continuity configuration data
1335 present error indication step
1340 test sample step
1350 process result signal step
1360 display indication of analyte step
1410 data processing system
1420 peripheral system
1430 user interface system
1440 data storage system
θ, φ angle The invention is inclusive of combinations of the aspects described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. An electrical connector adapted to receive a first substrate of a selected width, the first substrate having a plurality of conductive tracks disposed over a face surface of the first substrate, the electrical connector comprising:
   a) a housing comprising:
      i) a port; and
      ii) at least one first alignment feature spaced apart from the port to define a direction of permitted insertion of the first substrate into the electrical connector;
   b) at least three function pins mounted to the housing, each said function pin having a respective contact arranged to electrically connect to a respective one of the plurality of conductive tracks of the first substrate inserted in the electrical connector, the respective contacts being arranged between the port and the at least one first alignment feature in the direction of permitted insertion;
   c) a sense pin mounted to the housing, the sense pin having a contact adapted to electrically connect to at least one of the plurality of conductive tracks of the first substrate when inserted a predetermined distance into the electrical connector; and
   the sense pin further including a plurality of electrically-connected segments, at least one of said segments being mechanically mounted to the housing, each said segment extending substantially parallel or substantially perpendicular to the direction of permitted insertion of said first substrate,
   wherein the contact of said sense pin is arranged farther from said port than the respective contact of at least one of the at least three function pins.

2. An electrical connector adapted to receive a first substrate of a selected width, the first substrate having a plurality of conductive tracks disposed over a face surface of the first substrate, the electrical connector comprising:
   a) a housing comprising:
      i) a port; and
      ii) at least one first alignment feature spaced apart from the port to define a direction of permitted insertion of the first substrate into the electrical connector;
   b) at least three function pins mounted to the housing, each said function pin having a respective contact arranged to electrically connect to a respective one of the plurality of conductive tracks of the first substrate inserted in the electrical connector, the respective contacts being arranged between the port and the at least one first alignment feature in the direction of permitted insertion;
   c) a sense pin mounted to the housing, the sense pin having a contact adapted to electrically connect to at least one of the plurality of conductive tracks of the first substrate when inserted a predetermined distance into the electrical connector; and
   the sense pin further including a plurality of electrically-connected segments, at least one of said segments being mechanically mounted to the housing, each said segment extending substantially parallel or substantially perpendicular to the direction of permitted insertion of said first substrate,
   wherein the at least one first alignment feature includes a guiding surface and a retaining surface disposed along the direction of permitted insertion, the guiding surface forming an acute angle with the direction of permitted insertion and the retaining surface being substantially parallel to the direction of permitted insertion.

3. A system for detecting an analyte in a bodily-fluid sample, said system comprising:
   a) a controller;
   b) a test strip having a sample-receiving chamber and a plurality of conductive tracks electrically discontinuous from each other, each conductive track arranged at least partially on a first side of said test strip and at least partially adjacent to the sample-receiving chamber;
   c) an electrical connector comprising:
      i) a housing with a port adapted to receive the test strip inserted in a direction of permitted insertion;
      ii) three or more function pins mounted to the housing, each said function pin having a respective contact arranged to electrically connect to a respective one of the plurality of conductive tracks of the test strip inserted in the electrical connector; and
      iii) a sense pin mounted to the housing and having a contact adapted to electrically connect to one of the respective ones of the plurality of conductive tracks of the test strip inserted in the electrical connector, the contact of said sense pin being arranged opposite the port along the direction of permitted insertion;
   d) a continuity sensor adapted to detect an electrical connection between the sense pin and at least one of the function pins and provide an indication of which function pin(s) are electrically connected to the sense pin; and
   e) a storage unit storing a selected continuity configuration and a corresponding selection of two or more of the function pins;

wherein the controller is adapted to automatically:
i) in response to the continuity sensor, compare the provided indication to the stored selected continuity configuration; and
ii) if the provided indication corresponds to the stored selected continuity configuration, activate the ones of the function pins indicated by the stored corresponding selection to apply a test electrical signal across the sample-receiving chamber, and measure a result electrical signal to detect the analyte in the sample-receiving chamber.

4. The system according to claim 3, wherein the controller is further adapted to present an error indication if the provided indication does not correspond to the stored selected continuity configuration.

5. The system according to claim 3, wherein the storage unit stores a plurality of selected continuity configurations and respective corresponding selections of two or more of the function pins, and the controller is further adapted to:
i) compare the provided indication to each of the stored selected continuity configurations; and
ii) if the provided indication corresponds to one of the stored selected continuity configurations, activate the ones of the function pins indicated by the stored respective corresponding selection, so that an electrical signal is applied across the sample-receiving chamber to detect the analyte in the sample-receiving chamber.

6. The system according to claim 3, wherein:
a) the bodily-fluid sample is whole blood;
b) the stored corresponding selection specifies that two sets of at least two of the function pins each be activated; and
c) the controller is adapted to apply the test electrical signal by applying a glucose-measurement signal across the function pins in the first set and applying a hematocrit-measurement signal across the function pins in the second set.

7. The system according to claim 6, wherein the first set includes three of the function pins and the controller applies the glucose measurement signal between a first of the three of the function pins and a second of the three of the function pins, and also between a third of the three of the function pins and the second of the three of the function pins.

8. The system according to claim 3, wherein the electrical connector further includes two alignment features arranged so that the respective contacts of the function pins and the sense pin are between the port and each of the alignment features in the direction of permitted insertion.

9. The system according to claim 3, wherein the sense pin includes a plurality of electrically-connected segments, at least one of said segments being mechanically mounted to the housing, each said segment extending substantially parallel or substantially perpendicular to the direction of permitted insertion.

10. The electrical connector according to claim 3, wherein the sense pin does not include any segment extending other than substantially parallel or substantially perpendicular to the direction of permitted insertion.

11. The system according to claim 3, wherein the electrical signal is a voltage and the controller is further adapted to measure a current between the two of the conductive tracks to detect the analyte.

12. A method for determining an analyte in a bodily-fluid sample, the method comprising:
receiving an analytical test strip using a electrical connector of a test meter such that at least three conductive tracks exposed on a first side of the analytical test strip make electrical contact with respective function pins of the electrical connector and at least one of the conductive tracks further makes electrical contact with a sense pin of the electrical connector, the analytical test strip including a sample-receiving chamber adapted to receive the bodily-fluid sample;
sensing, using a controller of the test meter, electrical continuity between the sense pin and a first one of the function pins;
when continuity is sensed, the controller comparing an identity of the first one of the function pins to stored continuity-configuration information;
if the identity of the first one of the function pins corresponds to the stored continuity-configuration information, the controller automatically applying a selected electrical signal to selected ones of the function pins indicated by the stored continuity-configuration information and measuring a result electrical signal; and
the controller automatically processing the result electrical signal to detect whether a bodily-fluid sample has been applied to the sample-receiving chamber and, if so, to determine the analyte in the applied bodily-fluid sample.

13. The method according to claim 12, wherein the analyte is glucose and the bodily-fluid sample is a whole blood sample.

14. The method according to claim 12, further including presenting an indication of the determined analyte on a display.

15. The system according to claim 12, further including the controller automatically presenting an error indication if the identity of the first one of the function pins does not correspond to the stored continuity-configuration information.

16. The system according to claim 12, wherein the comparing step includes the controller automatically comparing the identity of the first one of the function pins to each of a plurality of stored values of continuity-configuration information, and if the identity matches one of the plurality, the controller automatically applying a selected electrical signal to selected ones of the function pins indicated by the matching stored values of the continuity-configuration information.

17. An electrical connector adapted to receive a first substrate of a selected width, the first substrate having a plurality of conductive tracks disposed over a face surface of the first substrate, the electrical connector comprising:
a) a housing comprising:
i) a port; and
ii) at least one first alignment feature spaced apart from the port to define a direction of permitted insertion of the first substrate into the electrical connector;
b) at least three function pins mounted to the housing, each said function pin having a respective contact arranged to electrically connect to a respective one of the plurality of conductive tracks of the first substrate inserted in the electrical connector, the respective contacts being arranged between the port and the at least one first alignment feature in the direction of permitted insertion; and
c) a sense pin mounted to the housing, the sense pin having a contact adapted to electrically connect to at least one of the plurality of conductive tracks of the first substrate when inserted a predetermined distance into the electrical connector;
wherein said contact of said sense pin is arranged between said respective contacts of two of said at least three function pins in a direction substantially perpendicular to the direction of permitted insertion.

* * * * *